(12) United States Patent
Ye et al.

(10) Patent No.: US 12,144,641 B2
(45) Date of Patent: Nov. 19, 2024

(54) METHOD FOR SIMULTANEOUS MULTIPLE MAGNETIC RESONANCE PARAMETER MAPPING OF LIVER

(71) Applicant: Zhejiang University, Hangzhou (CN)

(72) Inventors: Huihui Ye, Hangzhou (CN); Zijing Zhang, Hangzhou (CN); Huafeng Liu, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 128 days.

(21) Appl. No.: 18/120,988

(22) Filed: Mar. 13, 2023

(65) Prior Publication Data

US 2023/0210446 A1 Jul. 6, 2023

Related U.S. Application Data

(63) Continuation-in-part of application No. PCT/CN2022/134310, filed on Nov. 25, 2022.

(30) Foreign Application Priority Data

Nov. 29, 2021 (CN) .......................... 202111447712.4

(51) Int. Cl.
*A61B 5/00* (2006.01)
*A61B 5/055* (2006.01)
*G01R 33/561* (2006.01)

(52) U.S. Cl.
CPC ............ *A61B 5/4244* (2013.01); *A61B 5/055* (2013.01); *G01R 33/5616* (2013.01)

(58) Field of Classification Search
CPC ............ G01R 33/5616; G01R 33/5615; G01R 33/56–561; A61B 5/055; A61B 5/4244
See application file for complete search history.

(56) References Cited

U.S. PATENT DOCUMENTS

2019/0162807 A1* 5/2019 Zahneisen .......... G01R 33/5616

FOREIGN PATENT DOCUMENTS

WO WO-2022212244 A1 * 10/2022 ............. G01R 33/50

OTHER PUBLICATIONS

Zhang, Zijing, et al. "Liver-Buda-Sage: Simultaneous Whole Liver T 2 and T 2 Mapping in one Breath-Hold." 2022 IEEE 19th International Symposium on Biomedical Imaging (ISBI). IEEE, 2022.*

(Continued)

*Primary Examiner* — Carolyn A Pehlke
(74) *Attorney, Agent, or Firm* — MATTHIAS SCHOLL P.C.; Matthias Scholl

(57) ABSTRACT

The disclosure provides a modified EPI sequence for acquiring multi-shot and multi-echo images with interleaved blip-up and blip-down phase encoding; the blip-up and blip-down images are processed by topup in FSL to estimate the inhomogeneous main magnetic field $B_0$ map that causes image distortions; the $B_0$ map is then incorporated into the encoding matrix with a low rank constraint to form a joint reconstruction model; the joint reconstruction model is solved to obtain multiple distortion-free images; and the multiple distortion-free images are matched to dictionary to simultaneous acquire the quantitative $T_2(=1/R_2)$ and $T_2^*$ ($=1/R_2^*$) maps. In the phantom and in-vivo measurements, the disclosed method rapidly acquires the comparable quantitative images within one hold-breath (for 20 s) to the conventional mapping method, thus providing important practical application value for evaluation of liver damage, iron level and cancer lesion.

7 Claims, 6 Drawing Sheets

(56) References Cited

OTHER PUBLICATIONS

Ostenson, Jason. Magnetic Resonance Fingerprinting for Rapid Quantitative Imaging of the Liver. Diss. 2020.*

* cited by examiner

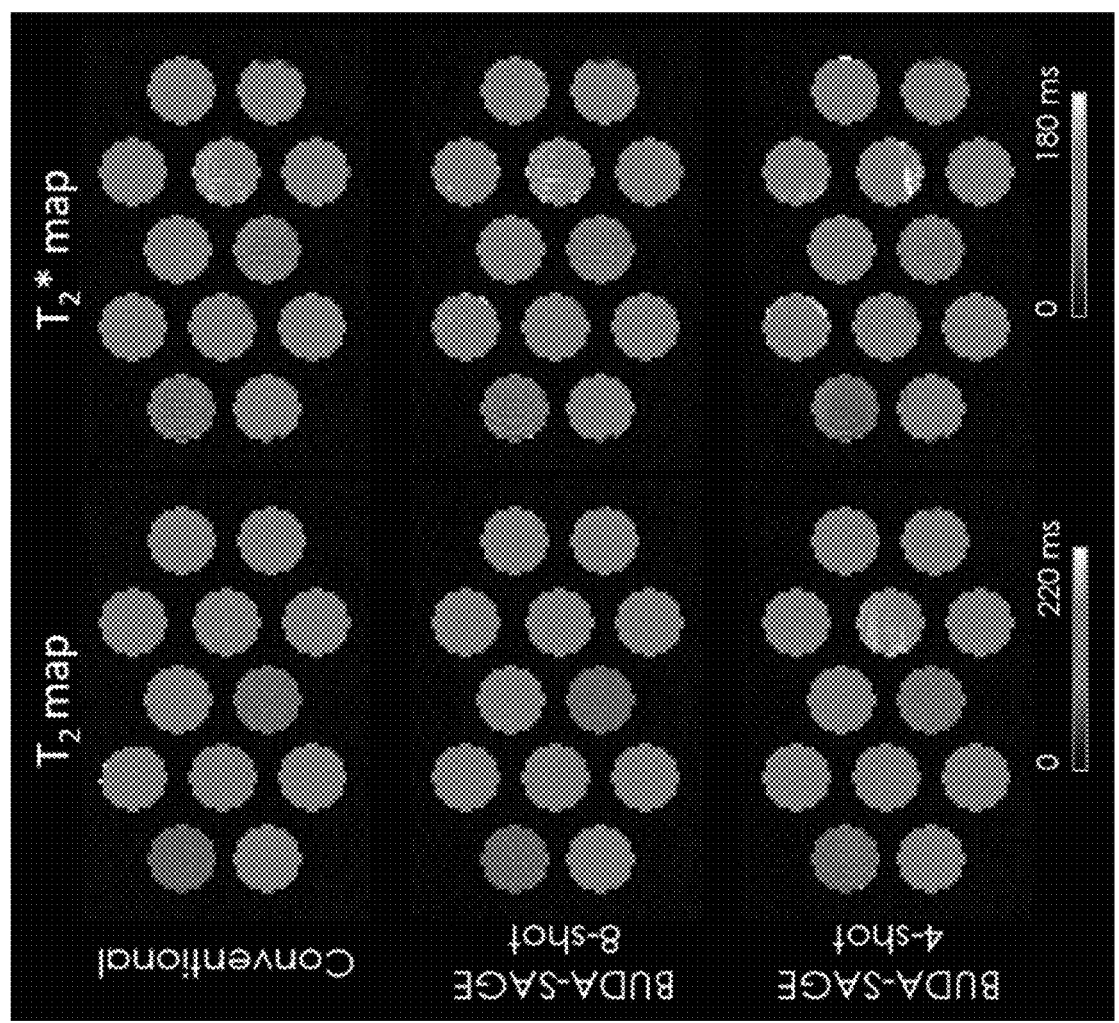

METHOD FOR SIMULTANEOUS MULTIPLE MAGNETIC RESONANCE PARAMETER MAPPING OF LIVER

CROSS-REFERENCE TO RELATED APPLICATIONS

This application is a continuation-in-part of International Patent Application No. PCT/CN2022/134310 with an international filing date of Nov. 25, 2022, designating the United States, now pending, and further claims foreign priority benefits to Chinese Patent Application No. 202111447712.4 filed Nov. 29, 2021. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, MA 02142.

BACKGROUND

The disclosure relates to the field of magnetic resonance imaging (MRI), and more particularly, to a method for quantitative multi-parameter mapping of whole liver.

Quantitative magnetic resonance imaging is an emerging non-invasive imaging method that aids in diagnosis of multiple liver diseases; for example, the method uses $T_2$ maps to assess the severity of the associated liver damage, and uses $T_2$ and $T_2^*$ maps to measure the iron content in the liver. Multi-parameter mapping (MPM) in quantitative MRI is used to monitor different pathophysiological characteristics of the diseases, thereby providing great diagnostic and prognostic value.

MPM typically involves monitoring signal intensities variation in multi-contrast weighted images, which thus takes a long time to acquire the multiple images, limiting the use in clinical setting and research. In conventional quantitative imaging methods, multiple different imaging sequences with different settings are typically scanned and used to estimate each of the multiple quantitative parameters. For example, a classical spin-echo sequence is used to acquire multiple spin echo signals at different echo times (TEs), to estimate a $T_2$ map; a classical multi-and-gradient-echo sequence is used to acquire gradient echo signals at different TEs, to estimate a $T_2^*$ map. The patients are instructed to hold their breath for a long time several times during multiple scans to reduce the motion induced artifact. With this, patients may feel tired, and position mismatch between the multiple quantitative parameters may occur.

Therefore, it is necessary to provide a method for rapidly imaging the liver with multiple parameters. Magnetic resonance fingerprinting is a method that can simultaneously quantify multiple MR parameters of one slice of liver within a single breath hold, and whole liver coverage acquisition will require multiple breath holds, hindering its uses in clinical practice.

SUMMARY

The disclosure is to provide a method for simultaneous multi-parameter mapping of whole liver in one scan.

The method comprises:
(1) modifying the echo-planar-imaging (EPI) sequence according to the required quantitative multi-parameter maps of liver tissue to be measured; wherein the multiple parameters comprise transverse relaxation time $T_2$ and effective transverse relaxation time $T_2^*$;
(2) importing the modified EPI sequence into a magnetic resonance imaging (MRI) scanner; using the MRI scanner to scan the liver in the body within one breath-hold, thus obtaining raw k-space data for each slice of the liver scanned at each echo time;
(3) processing the raw k-space data by a parallel imaging method (such as SENSE or MUSSELS) to obtain images acquired at each echo time;
(4) extracting image pairs with opposite phases encoding directions to estimate the inhomogeneous main magnetic field $B_0$ map that causes image distortion; incorporating the $B_0$ map into an encoding matrix with a low rank constraint to form a joint reconstruction model; and solving the joint reconstruction model to obtain reconstructed images of multiple slices of the liver scanned at each echo time;
(5) determining the dynamic range and step size of the quantitative parameters; and using the Bloch equation to form a dictionary that stores information about echo signals over time; and
(6) matching the reconstructed images pixelwise in 4) with the corresponding echo signal stored in the dictionary, so as to identify each pixel by specific values of the quantitative parameters, thus obtaining a quantitative multi-parameter map.

In a class of this embodiment, in 1), the EPI sequence comprises a series of events: two excitation pulses P1 and P2 of different flip angles in an interleaved manner; repetition time (TR) is a term for the timespan between successive excitation pulses P1; a gradient-echo, a spin-echo, and a mixed-spin-and-gradient-echo are generated during each TR; the excitation pulse P2 is applied between the gradient-echo and mixed-echo; and the echoes of adjacent TRs have opposite phase encoding directions.

In a class of this embodiment, in 1), the EPI sequence is jointly acquired by msBUDA and SAGE; where, msBUDA is a multi-shot EPI method that acquires two successive shots of data with opposite phase encoding directions, so that the images pairs with geometric distortions that are equal but in opposite directions are obtained and used to estimate the inhomogeneous main magnetic field $B_0$ map that causes image distortion; SAGE is a data acquisition method in which additional EPI readouts for spin-echo, gradient-echo, and mixed-spin-and-gradient-echo are added into the EPI sequence in each TR.

In a class of this embodiment, the image pairs corresponding to the two opposite phase-encoding directions are processed by topup in FSL to estimate the inhomogeneous main magnetic field $B_0$ map.

In a class of this embodiment, the joint reconstruction model is described as follows:

$$\min_x \sum_{s=1}^{N_s} \|F_s W_s C x_s - d_s\|_2^2 + \lambda \|H(x)\|_*$$

where, $F_s$ is the under-sampled Fourier operator in the $s^{th}$ shot; $W_s$ is the distortion operator (based on the inhomogeneous main magnetic field $B_0$ map estimated by topup in FSL) in the $s^{th}$ shot; $N_s$ is the total number of shots; C is the coil sensitivity map estimated from the distortion-free GRE data; $x_s$ is the reconstructed images in the $s^{th}$ shot; $d_s$ is the k-space data of the sin shot; $\| \ \|_2$ means Euclidean norm; $\| \ \|_*$ means nuclear norm; $\lambda$ is the weighting coefficient; x is a set of all $x_s$; and $\|H(x)\|_*$ enforces low-rank prior on the block-Hankel representation of the blip-up and blip-down data.

In a class of this embodiment, in 4), the joint reconstruction model is solved using iterative projection onto convex sets (POCS) to obtain the reconstructed images of multiple slices of the liver scanned at each echo time; iteration is alternated between data consistency and low-rank truncation, and ceases when the tolerance of root mean square error (RSME) between two successive iterations is less than 0.01%.

In a class of this embodiment, the Bloch equation is as follows:

$$S(t) = \begin{cases} S_0^I e^{-t \cdot R_2^*}, & 0 < t < T/2 \\ S_0^{II} e^{-T \cdot (R_2^* - R_2)} e^{-t(2R_2 - R_2^*)}, & T/2 < t < T \end{cases}$$

where, $S(t)$ is an MRI signal acquired at echo time t; T is the echo time of the spin echo, $S_0^I$ is an initial signal generated by a 90° pulse, $S_0^{II}$ is a superposition of initial signals generated by a 90° pulse and a 180° pulse; $R_2 = 1/T_2$, $R_2^* = 1/T_2^*$; the parameter $\delta$ is in the range of 1.00-1.82.

The disclosure provides a modified EPI sequence with multi-shots and multi-echoes with interleaved blip-up and blip-down phase encoding acquisition; the blip-up and blip-down images are processed by topup in FSL to estimate the inhomogeneous main magnetic field $B_0$ map that causes image distortions; the $B_0$ map is incorporated into the encoding matrix with a low rank constraint to form a joint reconstruction model; the joint reconstruction model is solved to obtain multiple distortion-free images; and the multiple distortion-free images are matched to dictionary to acquire the quantitative $T_2(=1/R_2)$ and $T_2^*(=1/R_2^*)$ maps. In the phantom and in-vivo measurements, the disclosed method rapidly acquires the comparable quantitative images within one hold-breath (for 20 s) to the conventional mapping method, thus providing important practical application value for evaluation of liver damage, iron level and cancer lesion.

BRIEF DESCRIPTION OF THE DRAWINGS

FIG. 2A are quantitative $T_2$ and $T_2^*$ maps obtained using different methods in phantom measurement according to one example of the disclosure; where the different methods comprise CMM, Protocol 1 (BUDA-SAGE 8-shot) and protocol 2 (BUDA-SAGE 4-shot);

DETAILED DESCRIPTION

To further illustrate the disclosure, embodiments detailing a method for simultaneous multi-parameter mapping of whole liver in one scan are described below. It should be noted that the following embodiments are intended to describe and not to limit the disclosure.

A method for simultaneous multi-parameter mapping of whole liver in one scan, and the method comprises:

S1. Sequence Design for Multi-Shot Blip Up-Down Acquisition (msBUDA)

Figure 1A:
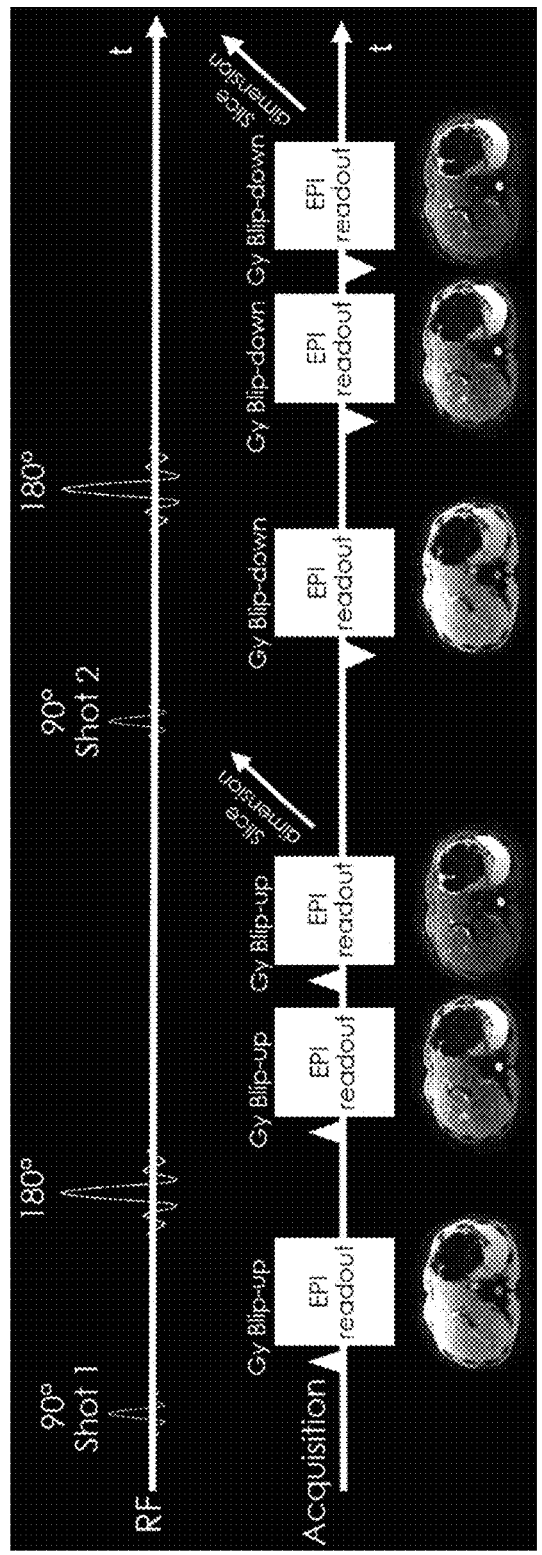
FIG. 1A is a schematic diagram of a liver-msBUDA-SAGE sequence according one example of the disclosure; where msBUDA and SAGE are used for data collection.

Referring to FIG. 1A, during MRI scan, MRI data is acquired with opposite phase encoding directions, i.e., with blips-up and blips-down, so as to generate images with geometric distortions that are equal but in opposite directions, thereby providing an inhomogeneous main magnetic field map that causes the geometric distortions.

S2. Sequence Design for Spin-And-Gradient Echo (SAGE) Imaging

Referring to FIG. 1A, additional EPI readouts for spin-echo, gradient-echo, and mixed-spin-and-gradient-echo are added into the EPI sequence to acquire multi-contrast images, thereby providing detailed information about quantitative multi-parameter MRI.

S3. MRI Scan by Liver-msBUDA-SAGE

During the MRI scan, patients are instructed to hold their breath, and raw k-space data for whole-liver multi-slice multi-contrast images are rapidly acquired at multiple echo times (TEs). Additionally, Protocol 1 and Protocol 2 are performed to validate the robustness of the disclosed method compared to the conventional single-parameter mapping method.

3.1 Phantom Validation

Protocol 1: the acquisition parameters are set as follows: in-plane resolution=1.5×1.5 $mm^2$, slice thickness=5 mm, matrix=330×220×80 $mm^3$, slice number=16, down-sampling factor (DSF)=4, partial Fourier=75%, repetition time (TR)=2.2 s, TE=12, 28, 48, 70, 80 and 102 ms. 4-shots of liver-msBUDA-SAGE with interleaved blip-up and blip-down phase encoding are collected, and the total acquisition time is 19.8 s.

Protocol 2: the acquisition parameters are the same as Protocol 1, except for DSF=8, partial Fourier=100%, TR=1.8 s, TE=12, 28, 48, 70, 80 and 102 ms, and the total data acquisition time=30.6 s.

Conventional mapping method (CMM): (1) To acquire a $T_2^*$ map, the parameters in a two-dimensional (2D) multi-echo gradient recalled echo (GRE) sequence are set as follows: resolution=1.5×1.5×5 $mm^3$, slice number=10, matrix=192×192×50 $mm^3$, TR=2.5 s, TE=3.55, 8.30, 13.05, 17.80, 22.55, 27.30, 32.05, 36.80, 41.55 and 46.30 ms, and the data acquisition time=2 min 40 s. (2) To acquire a $T_2$ map, the parameters in multi-slice single-spin-echo sequence are set as follows: resolution=1.5×1.5×5 $mm^3$, slice number=10, matrix=192×192×50 $mm^3$, TR=2.5 s, and the sequence is run six times with different TEs as follows: 10, 30, 50, 70, 90 and 110 ms, and the total data acquisition time=10.5 min.

3.2 In-Vivo Validation

A healthy volunteer was scanned with the approval of Institutional Review Board.

In in-vivo measurement, the parameters in the liver-msBUDA-SAGE sequence are the same as Protocol 1 and Protocol 2 in the phantom validation; notably, the volunteer is instructed to hold his/her breath during the MRI scan.

Conventional mapping method (CMM): To acquire a $T_2^*$-weighted image, the parameters in the 2D multi-echo GRE sequence are set as follows: resolution=1.5×1.5×5 mm³, slice number=16, matrix=336×216×80 mm³, TR=286 ms, TE=3.02, 6.67, 10.32, 13.97, 17.62, 21.27, 24.92, 28.57 and 32.22 ms; the data is acquired twice in a scan time of 32.6 s, each for 16.3 s; and the healthy volunteer is instructed to hold his/her breath for each data acquisition.

A 2D parameter-matched low-resolution GRE sequence was also used to obtain a distortion-free coil sensitivity map for subsequent liver-msBUDA-SAGE reconstruction.

S4. Liver-msBUDA-SAGE Reconstruction

Figure 1B:
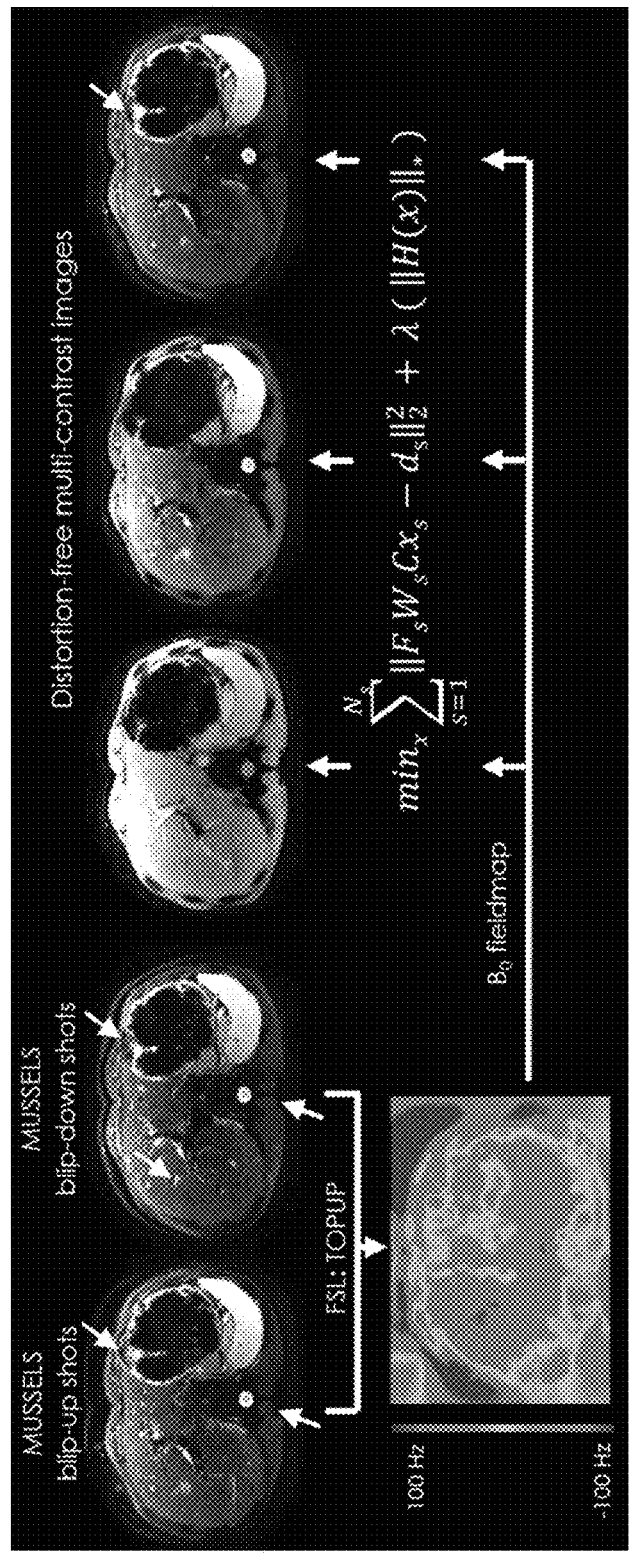
FIG. 1B is a schematic diagram of an algorithm based on a low rank constraint for reconstructing distortion-free multi-contrast images according to one example of the disclosure.

Referring to FIG. 1B, based on the raw k-space data obtained in S3, MUSSELS is used to reconstruct the blip-up and blip-down image pairs; the image pairs are processed by topup in FSL to estimate the inhomogeneous main magnetic field $B_0$ map that induces image distortions; the $B_0$ map is incorporated into an encoding matrix with a low rank constraint to form a joint reconstruction model. The joint reconstruction model is described as follows:

$$\min_x \sum_{s=1}^{N_s} \|F_s W_s C x_s - d_s\|_2^2 + \lambda \|H(x)\|_*$$

where, $F_s$ is the under-sampled Fourier operator in the $s^{th}$ shot; $W_s$ is the distortion operator (based on the inhomogeneous main magnetic field $B_0$ map estimated by topup in FSL) in the $s^{th}$ shot; C is the coil susceptibility map estimated from the distortion-free GRE data; $d_s$ is the k-space data of each shot; $\| \|_2$ means Euclidean norm; $\| \|_*$ means nuclear norm; $\lambda$ is the weighting coefficient; and $\|H(x)\|_*$ enforces low-rank prior on the block-Hankel representation of the blip-up and blip-down data.

The reconstruction is implemented using iterative projection onto convex sets (POCS); iteration is alternated between data consistency and low-rank truncation, and ceases when the tolerance of root mean square error (RSME) between two successive iterations is less than 0.01%.

S5. Quantitative Mapping Using the Multi-Contrast Weighted Images and Dictionary Matching.

A dictionary is created by discretizing the values of each parameter in the Bloch equation as follows:

$$S(t) = \begin{cases} S_0^I e^{-t \cdot R_2}, & 0 < t < T/2 \\ S_0^{II} e^{-T \cdot (R_2^* - R_2)} e^{-t(2R_2 - R_2^*)}, & T/2 < t < T \end{cases}$$

where, S(t) is the MRI signal acquired at echo time t, T is the echo time, $S_0^I$ is the initial signal generated by a 90° pulse, $S_0^{II}$ is the superposition of initial signals generated by a 90° pulse and a 180° pulse, $R_2$ (=1/$T_2$) is the reciprocal of the transverse relaxation time, $R_2^*$ (=1/$T_2^*$) is the reciprocal of the effective transverse relaxation time; the echo time T is equal to the spin-echo time t, smaller than the gradient-echo time t, and greater than the mixed-echo time t.

The dictionary is created as follows: $S_0^I$, $S_0^{II}$, $R_2$ (=1/$T_2$) and $R_2^*$ (=1/$T_2^*$) are estimated through a least-square solution of the Bloch equation from the reconstructed images in S4; from these estimates, an additional parameter $\delta = S_0^I/S_0^{II}$ is obtained; the range of the parameter $\delta$ was determined by the values estimated from iteration fit with the three parameters $\delta$, $R_2$ and $R_2^*$ to be 1.00-1.82 and is then discretized to one hundred values to form the dictionary; for each value of the parameter $\delta$, $T_2$ and $T_2^*$ values are discretized to form the MRI signal S based on the Bloch equation; the $T_2$ values are set as [1:1:50 52:2:150 155:5:250] and $T_2^*$ values are set as [1:1:50 52:2:150]; the discrete values and the Bloch equation are used to form the dictionary disclosed herein.

The quantitative $T_2$(=1/$R_2$) and $T_2^*$(=1/$R_2^*$) maps are obtained by matching the resulting distortion-free images in S4 with the dictionary.

Figure 2B:
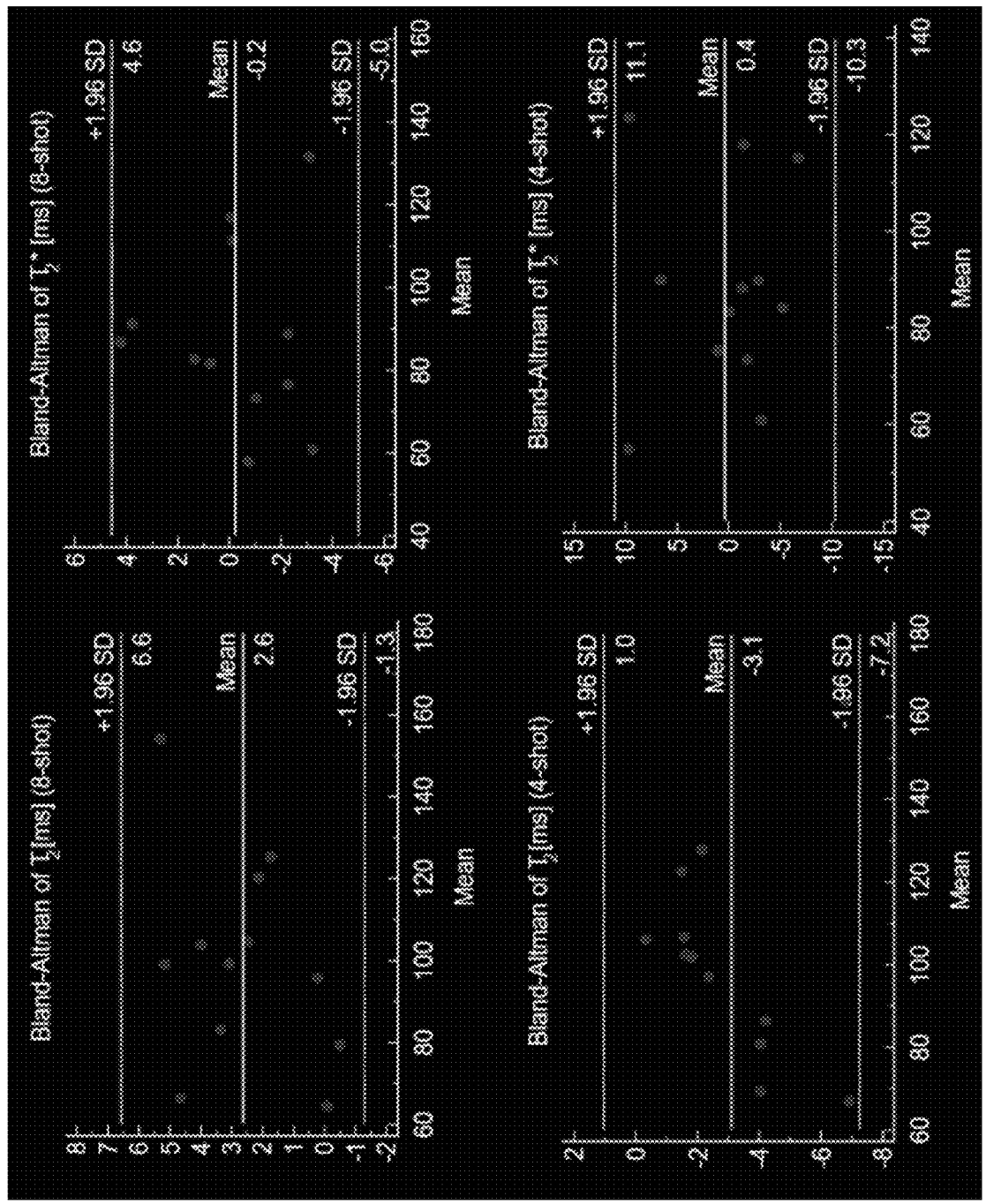
FIG. 2B are Bland-Altman plots showing the mean and difference for $T_2$ and $T_2^*$ values according to one example of the disclosure; where the first column shows the agreement between the $T_2$ and $T_2^*$ maps estimated from Protocol 1 and CMM; and the and second column shows the agreement between the $T_2$ and $T_2^*$ maps estimated from Protocol 2 and CMM.

The accuracy and robustness of $T_2$ and $T_2^*$ maps estimated from the disclosed method are verified on both the phantom and in-vivo data. FIG. 2A are quantitative $T_2$ and $T_2^*$ maps obtained using different methods in phantom; the different methods comprise CMM, Protocol 1 (BUDA-SAGE 8-shot) and protocol 2 (BUDA-SAGE 4-shot); FIG. 2B are Bland-Altman plots showing the mean and difference for the $T_2$ and $T_2^*$ values, where the first column shows the agreement between the $T_2$ and $T_2^*$ maps estimated from Protocol 1 and CMM; and the second column shows the agreement between the $T_2$ and $T_2^*$ maps estimated from Protocol 2 and CMM. Overall, good agreement is seen between the disclosed and conventional mapping methods, and the disclosed method presents good accuracy and robustness in phantom validation.

Figures 3A, 3B:
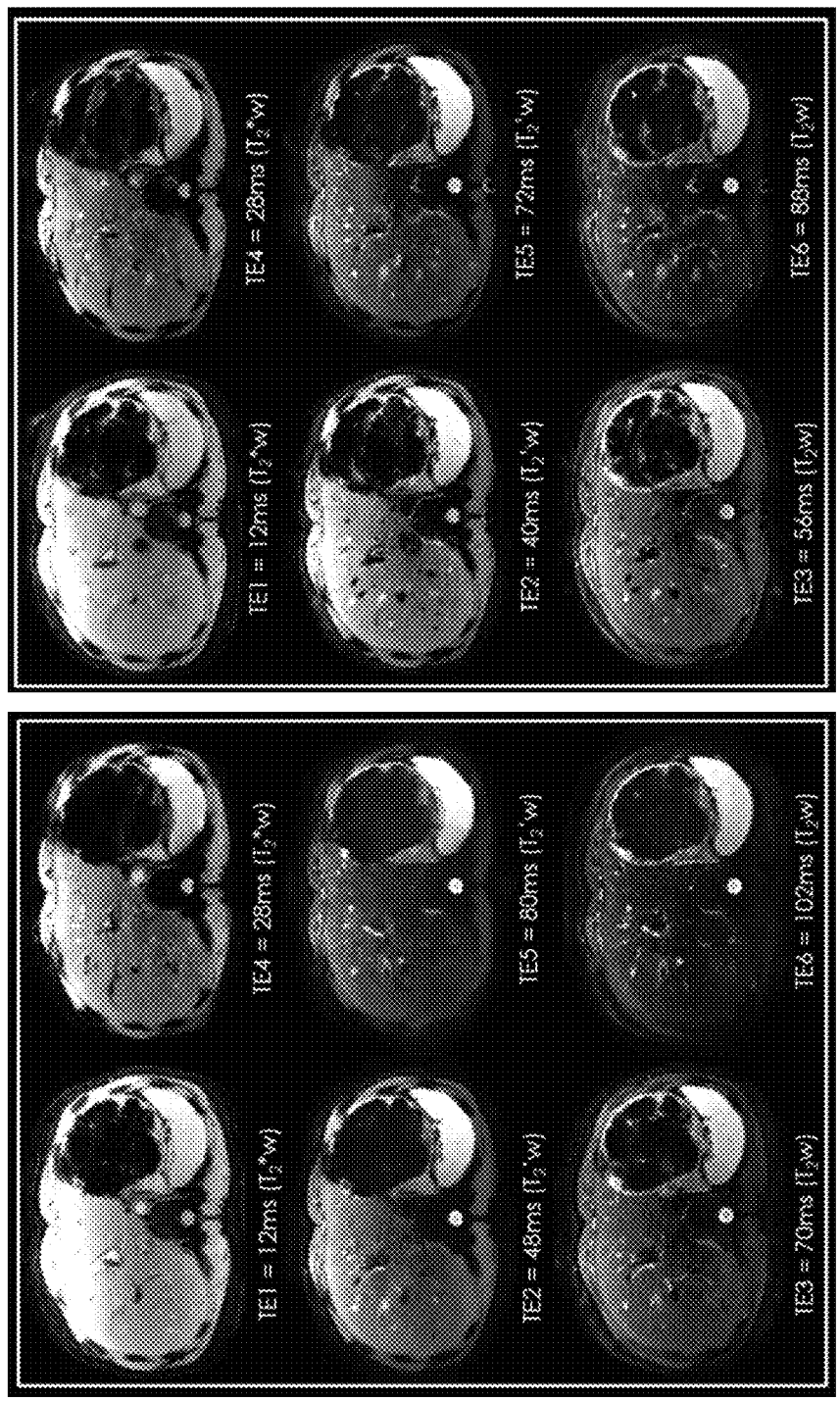
FIG. 3A are distortion-free multi-contrast images reconstructed by Protocol 1in in-vivo measurement according to one example of the disclosure.
FIG. 3B are distortion-free multi-contrast images reconstructed by Protocol 2 in in-vivo measurement according to one example of the disclosure.
Figure 4B:
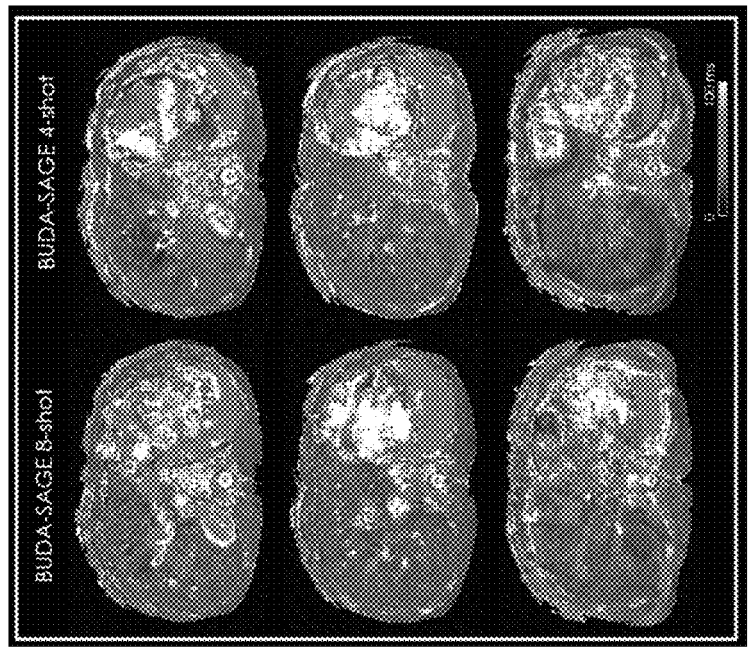
FIG. 4B are $T_2$ maps of the $3^{th}$, $7^{th}$, and $13^{th}$ liver slices in Protocol and Protocol 2 according to one example of the disclosure.
Figure 4A:
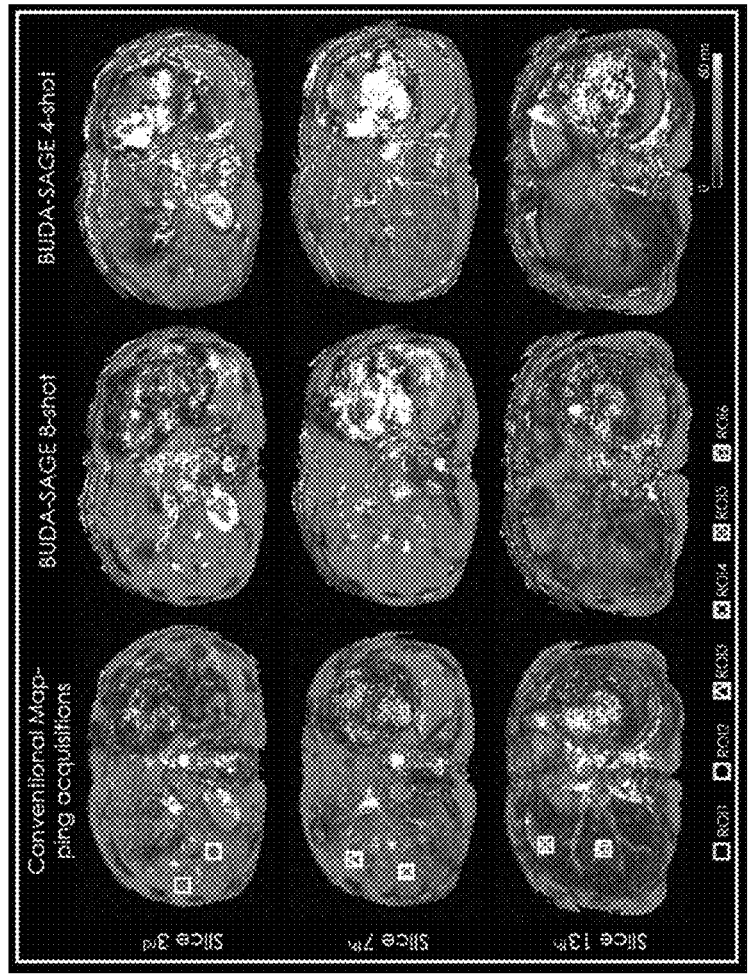
FIG. 4A are $T_2^*$ maps of the $3^{th}$, $7^{th}$, and $13^{th}$ liver slices in CMM, Protocol 1 and Protocol 2 according to one example of the disclosure; where six regions of interest (ROIs) from the slices were selected for statistical analysis.

FIGS. 3A and 3B are distortion-free multi-contrast images reconstructed by Protocol 1 and protocol 2 in in-vivo measurement. Overall, good agreement is seen between Protocol 1 and Protocol 2, indicating that the disclosed method presents good robustness in in-vivo measurement; the quantitative maps show comparable values to the conventional mapping method in in vivo measurement, offering good robustness. FIGS. 4A and 4B are $T_2^*$ and $T_2$ maps of the 3th, 7th, and 13th liver slices. Six regions of interest (ROIs) from the slices were selected for statistical analysis. As shown in Table 1, the disclosed method shows good agreement with the conventional mapping method, and the quantitative maps estimated from the disclosed method showed comparable accuracy and robustness to the conventional mapping method in in vivo measurement.

All experiments above were performed on a 3T Siemens Prisma MRI scanner; and the parameters described herein is defined as follows:

$T_2$ is the transverse relaxation time required for the transverse magnetization to decay to 37% of its initial value; the tissues are classified into short $T_2$ tissues (with short $T_2$ time: 1 ms≤$T_2$≤10 ms) and long $T_2$ tissues (with long $T_2$ time: 10 ms≤$T_2$).

$T_2^*$ is the effective transverse relaxation time required for the transverse magnetization to decay to 37% of its initial value due to the inhomogeneous magnetic field.

$B_0$ is the strength of the main magnetic field; in the figures, $B_0$ only shows the magnetic difference relative to the strength of the main magnetic field.

TE is the echo time that refers to the time from the center of the signal excitation to the center of the echo.

TR is the time between successive excitation pulses.

TABLE 1

| ROIs | $T_2^*$ (msec) | | | $T_2$ (msec) | |
|---|---|---|---|---|---|
| | Conventional method | Our method 4-shot | Our method 8-shot | Our method 4-shot | Our method 8-shot |
| ROI1 | 20.17 | 22.47 | 23.56 | 32.10 | 29.06 |
| ROI2 | 21.08 | 18.11 | 24.08 | 30.00 | 29.46 |
| ROI3 | 20.65 | 19.08 | 22.31 | 28.23 | 28.47 |
| ROI4 | 18.04 | 23.24 | 22.49 | 29.48 | 27.66 |
| ROI5 | 19.89 | 20.66 | 16.15 | 26.60 | 25.98 |
| ROI6 | 23.38 | 24.04 | 23.10 | 37.15 | 27.46 |
| All ROIs statistics | 20.54 ± 1.74 | 21.26 ± 2.37 | 22.01 ± 2.77 | 30.59 ± 3.70 | 28.01 ± 1.26 |
| Literature statistics | | 20 ± 5 | | | 31 ± 6 |
| | | 22.9 ± 5.1 | | | 344 |

It will be obvious to those skilled in the art that changes and modifications may be made, and therefore, the aim in the appended claims is to cover all such changes and modifications.

What is claimed is:

1. A method for quantitative multi-parameter mapping of whole liver in one scan, the method comprising:
    (1) modifying an echo-planar-imaging (EPI) sequence according to required quantitative multi-parameter maps of liver tissue to be measured;
    wherein multiple parameters comprise transverse relaxation time $T_2$ and effective transverse relaxation time $T_2$;
    (2) importing the modified EPI sequence into a magnetic resonance imaging (MRI) scanner; using the MRI scanner to scan the liver in the body within one breath-hold, thus obtaining raw k-space data for each slice of the liver scanned at each echo time;
    (3) processing the raw k-space data by a parallel imaging method to obtain images acquired at each echo time;
    (4) extracting image pairs with opposite phases encoding directions to estimate an inhomogeneous main magnetic field $B_0$ map that causes images distortions; incorporating the $B_0$ map into an encoding matrix with a low rank constraint to form a joint reconstruction model; and solving the joint reconstruction model to obtain reconstructed images of multiple slices of the liver scanned at each echo time;
    (5) determining a dynamic range and step size of the quantitative parameters; and using a Bloch equation to form a dictionary that stores information about echo signals over time; and
    (6) matching each pixel point in the reconstructed images pixelwise in 4) with a corresponding echo signal stored in the dictionary, so as to identify each pixel by specific values of the quantitative parameters, thus obtaining a quantitative multi-parameter map.

2. The method of claim 1, wherein in 1), the EPI sequence comprises a series of events: two excitation pulses P1 and P2 of different flip angles in an interleaved manner; repetition time (TR) is a term for a timespan between successive excitation pulses P1; a gradient-echo, a spin-echo, and a mixed-spin-and-gradient-echo are generated during each TR; the excitation pulse P2 is applied between the gradient-echo and mixed-spin-and-gradient-echo; and the echoes of adjacent repetition times have opposite phase encoding directions.

3. The method of claim 1, wherein in 1), the EPI sequence is jointly acquired by msBUDA and SAGE; where, msBUDA is a multi-shot EPI method that acquires two successive shots of data with opposite phase encoding directions, so that the images pairs with geometric distortions that are equal but in opposite directions are obtained and used to estimate the inhomogeneous main magnetic field $B_0$ map that causes image distortions; SAGE is a data acquisition method in which additional EPI readouts for spin-echo, gradient-echo, and mixed-spin-and-gradient-echo are added into the EPI sequence in each TR.

4. The method of claim 1, wherein the image pairs corresponding to the two adjacent echoes of the same type are processed by topup in FSL to estimate the inhomogeneous main magnetic field $B_0$ map.

5. The method of claim 1, wherein the joint reconstruction model is described as follows:

$$\min_x \sum_{s=1}^{N_s} \|F_s W_s C x_s - d_s\|_2^2 + \lambda \|H(x)\|_*$$

where, $F_s$ is an undersampled Fourier operator in the $s^{th}$ shot; $W_s$ is a distortion operator based on the inhomogeneous main magnetic field $B_0$ map estimated by topup in FSL in the $s^{th}$ shot; $N_s$ is a total number of shots; C is the coil sensitivity map estimated from the distortion-free GRE data; $x_s$ is the reconstructed images in the $s^{th}$ shot; $d_s$ is the k-space data of the $s^{th}$ shot; $\| \|_2$ means Euclidean norm; $\| \|_*$ means nuclear norm; $\lambda$ is a weighting coefficient; x is a set of all $x_s$; $\|H(x)\|_*$ and enforces low-rank prior on the block-Hankel representation of the blip-up and blip-down data.

6. The method of claim 1, wherein in 4), the joint reconstruction model is solved using iterative projection onto convex sets (POCS) to obtain the reconstructed images of multiple cross-sections of the liver scanned at each echo time; iteration is alternated between data consistency and low-rank truncation, and ceases when the tolerance of root mean square error (RSME) between two successive iterations is less than 0.01%.

7. The method of claim 1, wherein the Bloch equation is as follows:

$$S(t) = \begin{cases} S_0^I e^{-t \cdot R_2^*}, & 0 < t < T/2 \\ S_0^{II} e^{-T \cdot (R_2^* - R_2)} e^{-t \cdot (2R_2 - R_2^*)}, & T/2 < t < T \end{cases}$$

where, S(t) is a MRI signal acquired at echo time t; T is the echo time of a spin echo, $S_0^I$ is an initial signal produced by a 90° pulse, $S_0^{II}$ is a superposition of initial signals produced by a 90° pulse and a 180° pulse; $R_2 = 1/T_2$, $R_2^* = 1/T_2^*$; the parameter δ is in the range of 1.00-1.82.

* * * * *